United States Patent [19]

Allan

[11] Patent Number: 5,022,917
[45] Date of Patent: Jun. 11, 1991

[54] LIQUID HERBICIDALLY ACTIVE COMPOSITIONS

[75] Inventor: G. Graham Allan, Seattle, Wash.

[73] Assignee: Melamine Chemicals, Inc., Donaldsonville, La.

[21] Appl. No.: 478,729

[22] Filed: Feb. 12, 1990

Related U.S. Application Data

[63] Continuation of Ser. No. 671,731, Nov. 15, 1984, abandoned, which is a continuation-in-part of Ser. No. 518,281, Jul. 28, 1983, abandoned.

[51] Int. Cl.$^5$ ............................................. A01N 43/64
[52] U.S. Cl. ................................... 71/93; 71/DIG. 1
[58] Field of Search ................ 71/DIG. 1, 65, 79, 93, 71/117

[56] References Cited

U.S. PATENT DOCUMENTS

| | | | |
|---|---|---|---|
| 3,074,845 | 1/1963 | Geary | 71/65 |
| 3,223,513 | 12/1965 | Geary | 71/92 |
| 3,813,236 | 5/1974 | Allan | 71/94 |
| 3,983,116 | 9/1976 | Lin | 544/211 |
| 4,035,365 | 7/1977 | Kay | 544/211 |
| 4,060,404 | 11/1977 | Evans | 544/211 |
| 4,069,039 | 1/1978 | Evans | 544/211 |
| 4,082,536 | 4/1978 | Kay | 544/211 |
| 4,101,308 | 7/1978 | Ochomogo | 544/211 |
| 4,209,619 | 6/1980 | Albert | 544/211 |
| 4,283,387 | 8/1981 | Young et al. | 71/64 F |

FOREIGN PATENT DOCUMENTS 855166 9/1980 Belgium .

OTHER PUBLICATIONS

Yarborough, *Chemical Abstracts*, vol. 94 #97896y, 1981 "Hexazinone pellet for spot treatment of woody weeds in lowbush blueberry fields".

Lane, *Chemical Abstracts*, vol. 95 #182189k, 1981 "Control of certain hard to kill weed species in lucene with hexazinone".

G. G. Allan et al., "Selective Suppression of Weeds and Deciduous Brush in the Presence of Conifers", *International Pest Control*, vol. 14, No. 2, Mar./Apr. 1972.

G. G. Allan et al., "Phytoxicity of Some Systemic Insecticides to Spanish Cedar", *International Pest Control*, vol. 15, No. 1, Jan./Feb. 1973.

G. G. Allan et al., "Growth Enhancement of a Juvenile Conifer Forest Six Years After Application of a Controlled Release Herbicide", *International Pest Control*, vol. 20, No. 2, Mar./Apr. 1978.

G. G. Allan et al., "Controlled Release Growth Stimulants for Plants", *Biomedical Polymers: Polymeric Materials and Pharmaceuticals for Biomedical Use*, 1980.

*Primary Examiner*—Frederick E. Waddell
*Assistant Examiner*—Raymond Covington
*Attorney, Agent, or Firm*—Breiner & Breiner

[57] ABSTRACT

Liquid compositions provide a source of a herbicide or other biologically active substance in combination with a particular nitrogenous chemical, preferably melamine. After application, the herbicide is characterized by enhanced efficacy as compared to the efficacy observed when applied alone.

7 Claims, No Drawings

LIQUID HERBICIDALLY ACTIVE COMPOSITIONS

This is a continuation of application Ser. No. 671,731 filed Nov. 15, 1984 now abandoned; which in turn is a continuation-in-part of Ser. No. 518,281 filed July 28, 1983 now abandoned.

The subject matter of this application is related to that in commonly assigned U.S. patent application Ser. No. 305,603, filed Sept. 25, 1981, of Allan et al., which describes slow release fertilizer granules such as melamine-urea agglomerates and prills. The subject matter of this application is also related to that of commonly assigned U.S. patent application Ser. No. 305,394, filed Sept. 25, 1981, of Freepons, which is concerned with methods of applying slow release nitrogen fertilizer materials, such as melamine-based granules, to the soil.

These applications, referred to above, are all expressly incorporated herein by reference.

BACKGROUND OF THE INVENTION

1. Field of the Invention

This invention relates to liquid, preferably sprayable, compositions containing biologically active material, particularly those that are useful in agriculture. These compositions provide for the release and often for the sustained action of biologically active substances. More particularly, the invention relates to a preferably sprayable liquid product that is formulated with a biologically active substance such as a herbicide or other pesticide for use in crop production. This product can be applied to the soil or plant foliage using conventional equipment. Its composition is such as to provide prolonged activity or improved activity.

2. Description of the Prior Art

Melamine and its hydrolysis products, ammeline, ammelide, and cyanuric acid, and as well the related material dicyandiamide (cyanoguanidine), have often been considered as potential sources of nitrogen for incorporation in fertilizer compositions or for utilization as nitrogen sources per se. Melamine and dicyandiamide each have a nitrogen content of 66.67%; two-thirds of their weight is nitrogen. When used as fertilizer materials, they provide high percentages of nitrogen per unit weight applied.

Commercially produced melamine is available only as a fine crystalline powder, because small size particles are required for the present major commercial end markets for melamine. A typical screen analysis for one commercially available (from Melamine Chemicals, Inc.—MCI) dry melamine product, conducted with United States Standard Sieve screens, is as follows:

| Screen Analysis | Percent Retained |
| --- | --- |
| 40 Mesh | 0–0.1 |
| 40–50 Mesh | 0–0.1 |
| 50–60 Mesh | 0–0.3 |
| 60–80 Mesh | 0.5–5.0 |
| 80–100 Mesh | 1.0–5.0 |
| 100–200 Mesh | 13–30 |
| 200–325 Mesh | 13–30 |
| Thru 325 Mesh | 40–60 |

Other commercially available melamine products may be somewhat coarser, but the majority of the particles remain below 40 mesh. The smallest particles are very fine and powdery, and their sizes are difficult to measure. The fine particle sizes of commercial dry crystalline melamine, as currently produced, make it difficult to use as such, as a dry fertilizer material. An aqueous slurry of particulate melamine is suggested for use in the Freepons application, above, for dispensing into a trench, where the fine melamine particles can easily be covered by a layer of soil, so they will not blow away.

A somewhat related agricultural chemical problem is the formulation of biocides, plant growth regulants, and other biologically active materials for slow or controlled rate release, and for improved efficacy. Biocides include such pesticides as insecticides, herbicides, and fungicides. One basic purpose of prolonged activity formulations of biocides is to extend the time between repeat applications and thus effect a saving on the cost of the labor involved in an application. A second important purpose is to improve the effectiveness of a biocide by a sustained but more uniform activity over a period of time, rather than the inefficient technique of several applications of the biocide alone, over a period of time, with concomitant short periods of high biocide concentration and effectiveness together with the risk during such periods of pollution and phytotoxicity to crops, and long periods of low or zero concentration.

More prolonged activity for biologically active materials would permit extended time intervals between treatments and the reduction of the application level for a given effect over a period of time, thus reducing environmental impact. Thus, from an ecological standpoint, the controlled release of a pesticide, for example, if coupled with improved efficacy and a prolongation of effective activity, would enhance the lifetime of a nonpersistent agent at the site of treatment.

When only ferilizer is applied to slow growing crops such as trees, weeds that compete with tree seedlings may be stimulated to grow to such an extent as to crowd and compete with the seedlings. Thus the positive effects expected from fertilization may be negated by the vigorous growth of weeds that compete with the trees for vital water, light, and nutrients. Also, if fertilizer materials such as urea and/or ammonium salts are applied in sufficient quantity so that the effects can be observed over a significant period of time, not only is fertilization inefficient but also there may be toxic effects because of salt stress. Avoiding this by more frequent multiple, small applications generally is not practical for tree crops.

The controlled release of biocides has previously been achieved by their incorporation within a matrix of a synthetic polymer, e.g., encapsulation wherein for example a pest control agent is surrounded by an enveloping wall of a synthetic polymer that permits loss through diffusion, permeation or degradation; dispersion of the pesticide in an elastomer or a synthetic plastic wherein the pesticide is released through leaching or diffusion; or chemical combination of the pesticide with a high molecular weight synthetic polymer in such a manner that the appended pesticide is slowly released from the polymeric backbone upon exposure to the pest infested environment. However, the prior art approaches often fall short of what is desired, in one or more respects. Also, they tend to be expensive, and some of the synthetic polymeric materials suggested for use are either not biodegradable or degrade so slowly that it is not a useful property.

Some sustained action, biologically active compositions, such as insecticides, fungicides, herbicides, nematocides, and other biocides, and plant growth regulators, are disclosed in U.S. Pat. No. 3,074,845 to Geary. The biologically active material is formulated with an inert carrier material and an amido-aldehyde resin. The formulation is prepared by first impregnating the inert carrier material with the biologically active substance, coating the impregnated carrier material with the amido-aldehyde resin, and then polymerizing the resin in situ. Suitable resins include urea-formaldehyde, melamine-formaldehyde, and urea-melamine-formaldehyde resins.

A later Geary patent, U.S. Pat. No. 3,223,513, discloses similar sustained release compositions in which the biologically active material is mixed with monomeric amido and monomeric aldehyde reactants, and then the reactants are polymerized to form an amidoaldehyde resin in situ. When the biologically active material and the resin-forming reactants are combined, an occlusion of the active material with the resin is obtained, which in physical form is sieve-like or spongelike in structure with the molecules of active material in the interstices of the polymer.

Belgian Pat. No. 885,166, of Allan (the applicant herein), discloses a simple physical mixture of fine particles of (1), melamine that has been recrystallized to remove certain phytotoxic impurities and (2), a controlled release form of 2,4-dichlorophenoxyacetic acid (2,4-D). The preferred controlled release form of 2,4-D is prepared by intimately mixing or melting together equal parts by weight of kraft lignin and 2,4-D and extruding the resulting mixture in pellet or flake form of the desired size.

More recently, U.S. Pat. No. 4,283,387 to Young et al. discloses controlled release biologically active compositions similar to those disclosed in the later Geary patent mentioned above. In Young et al., a mixture comprising a carbinol-containing organic polymer, crosslinking agents for the polymer, and a biologically active substance undergoes hydrolysis to form a polymeric network capable of controlling the release of the biologically active substance.

A different approach appears in Pierce, 3,172,752. In one embodiment, a herbicide, fungicide, or insecticide is mixed with activated sewage sludge. The mixture is then adsorbed into pores, some of which are capillary, in particles of expanded perlite. The particles are then sprayed with a urea-formaldehyde solution, which forms a very slowly soluble sheath about each particle upon curing and drying.

SUMMARY OF THE INVENTION

In accordance with one embodiment of the present invention, liquid compositions are prepared that, after application, provide a source of a biologically active substance (BAM) characterized by enhanced efficacy, as compared to the efficacy that is observed when the BAM is applied alone, or when applied together with commonly used soluble nitrogen fertilizers, such as urea.

One broad concept of the invention is that a biologically active material (BAM), when made up in intimate admixture with a high nitrogen source compound such as melamine, for example, into a liquid, preferably a sprayable liquid formulation, and applied appropriately, exhibits more prolonged and/or more effective activity. In place of melamine, other poorly soluble high nitrogen sources may be used, such as benzoguanamine, dicyandiamide, ammeline, ammelide, cyanuric acid, mixtures thereof, their and melamine's physiologically acceptable inorganic and organic salts, and mixtures thereof. Melamine and its salts are the preferred nitrogen source materials. These nitrogen sources generally are compounds in crystalline or powdered form.

The mechanism for achieving the enhanced efficacy is not fully understood. It is theorized, however, that there may be either a chemical reaction of some sort, or hydrogen bonding, or a combination of these, between the biologically active material and the nitrogen source material, particularly melamine, or a physiological response by the weed plant to the combined presence of the BAM and melamine (or the like). The data that is now available does not permit a definitive conclusion, but there appears to be an indication that with a given BAM, to achieve a specified result, the use of the present invention permits application of the BAM at a lower rate than is possible when the BAM is applied alone in a conventional vehicle.

It can also be theorized that the melamine or other poorly soluble nitrogen source has some kind of stimulatory or synergistic effect of a nature that cannot presently be explained. Whether that is the case or not, the slow release nitrogen material, over a period of time, does benefit plant life by slow conversion in the soil to a form in which it is useful to plant life growing in the soil. The biologically active material that is selected for use may be any such material that does not interfere with the dissolution of the nitrogen source and the action on it of microorganisms to produce nitrogen in a form that is of nutrient value to plant life.

Most generally, liquid formulations prepared in accordance with the invention will be in the form of slurries or suspensions. However, they may also be in the form of solutions.

In one preferred, broad embodiment of the invention, the sprayable formulation comprises at leased one biologically active material; a nitrogenous compound selected from the group consisting of melamine, benzoguanamine, dicyandiamide, ammeline, ammelide, cyanuric acid, mixtures thereof, and the physiologically acceptable salts thereof, both organic and inorganic; and a liquid vehicle in which these said components are dissolved and/or suspended, to form a liquid, preferably sprayable composition. The nitrogenous compound and the biologically active material are preferably present in such proportions that the ratio is at least 3:1, by weight.

In a more specific preferred embodiment of the invention, the liquid, preferably sprayable formulation is in the form of a liquid fertilizer composition having an aqueous vehicle. There are dissolved in the aqueous vehicle one or more sources of N, P, and K fertilizer values. The N source comprises at least one readily water soluble N source and at least one poorly water soluble high N source having a water solubility at 20° C., at pH 7, not above 5 grams per 100 grams of water. One useful such high N source is selected from the group consisting of melamine, benzoguanamine, dicyandiamide, ammeline, ammelide, cyanuric acid, mixtures thereof, and the physiologically acceptable salts thereof, both organic and inorganic. In addition, the composition may contain at least one emulsifying, suspending, or stabilizing agent, or it may be mechanically agitated. It also contains at least one biologically active material at a concentration that is useful, upon application of the liquid fertilizer, to perform its intended function. Following application of the composition to a substrate, such as the soil, it is characterized by more prolonged activity of the biologically active material than would be the case of it alone had been applied.

The efficacy of the biologically active material is improved, although the theoretical reason for this is not understood at the present time. Efficacy may be enhanced as a result of a physiological or biochemical response by the weed, insect, or other pest to the simultaneous presence of the pesticide and the melamine or other poorly soluble nitrogenous source as specified above, with which it was intimately brought into contact for application. Such a physiological or biochemical response by the weed, insect or other pest would presumably take place within the weed, insect, or other pest following uptake, absorption, inhalation or ingestion.

For example, certain grassy and herbaceous weeds have been observed to be less tolerant of, that is, more sensitive to, a specific triazine herbicide when that herbicide has been applied together with melamine, than when applied alone or with a highly soluble nitrogen fertilizer such as urea. This reduced tolerance for, or greater sensitivity to, a herbicide may manifest itself in one or more of several ways: earlier weed kill; higher initial kill; more chlorosis of the surviving weeds; and/or prolonged duration of kill of newly germinating weed seeds.

DEFINITIONS

The term "biologically active material" (BAM) is used in a broad sense to refer to any of the common biologically active substances in common use, for example, in agricultural and turf grass treatment chemical applications. Thus the biologically active material (BAM) could be a herbicide, insecticide, fungicide, fumigant, miticide, nematocide, or other form of biocide, or a plant growth regulator, a repellent, a rodenticide, or the like.

The term "granular" is employed herein in a broad sense, to refer to granular products produced from particles and a binder for the particles. The binder is settable and initially may be molten, to harden on setting, or moist, requiring drying for setting. Agglomerated granules may be formed by a binder that is applied as an aqueous solution, and dried to cause binding. Urea and similar fusible binders may be applied while molten, and typically produce very strong granules. Screening and recycling may be used to achieve desired sizes. Granules may also be formed by mixing fine particles in a molten binder material, then chilling the mixture. The mixture may be chilled in block form then shaved, or comminuted; it may be drum chilled and flaked; or drops of the mixture may be chilled. The term "granular" most often is used in connection with generally spherically shaped materials, but also encompasses such products having other shapes, such as flakes and shavings.

The term "dispersed" is used to mean distributed, and is intended to encompass suspended, dissolved, and both suspended and dissolved substances. The term "poorly water soluble" refers to materials that dissolve in water at 20° C., pH 7, to the extent of 5 grams per 100 grams, or less; that is, materials that form solutions of 5% or less concentration.

The term "slightly water soluble" refers to materials that dissolve in water at 20° C., pH 7, to the extent of 1 gram per 100 grams or less; that is, materials that form solutions of 1% or less concentration.

The term "readily water soluble" refers to materials that dissolve in water at 20° C., pH 7, to the extent of 20 grams per 100 grams or more, that is, materials that form solutions of 16% or greater concentration.

Similar terms should be understood to have similar meanings. For example, the expression "poor water solubility" is used to refer to materials that are "poorly water soluble", as defined above.

Based on available information, the solubilities in water at 20° C., pH 7, for several materials useful in connection with this invention, in grams per 100 grams of water are:

TABLE 1

| Material | Solubility (g/100 g) |
|---|---|
| Melamine | 0.50 |
| Benzoguanamine | 0.06 (22° C.) |
| Dicyandiamide | 2.26 (at 13° C.) |
| Ammeline | 0.008 |
| Ammelide | less than 0.008 |
| Cyanuric Acid | 0.27 |
| Melamine Nitrate | 0.85 |
| Ammonium Nitrate | 192 |
| Ammonium Sulfate | 75.4 |
| Diammonium Phosphate | 131 (at 15°) |
| Potassium Acid Sulfate | 51.4 |
| Potassium Sulfate | 11.1 |
| Urea | 119.3 (at 25° C.) |

In referring to particle sizes, the term "diameter" is used, as it commonly is, to refer to the largest dimension of a particle, even though the particle is not spherical in shape.

DESCRIPTION OF THE PREFERRED EMBODIMENT

In a very simple formulation that embodies the invention, a sprayable liquid formulation comprises a biologically active material (BAM), such as, for example, a material exhibiting herbicidal activity. Such a material may have one or several active ingredients, depending upon its intended purpose. The formulation also includes a nitrogenous compound that, generally, is poorly water soluble, as defined above. Preferably, the nitrogenous compound is a triazine, and most preferably, it is melamine or ammeline. A third essential component is a liquid vehicle in which the other components are suspended, dissolved, or both suspended and dissolved. An emulsifying, suspending or stabilizing agent, or a combination of these, may be present in the liquid vehicle to facilitate handling, storage, shipment and use.

While not wishing to be bound by any particular theory, it appears that there is a form of chemical reaction, or hydrogen bonding, or a combination of these, between the nitrogenous compound and the biologically active material. Whether this is so or not, the nitrogenous material exhibits an observable effect on the biological activity after the formulation has been applied. This effect may be to render the BAM, such as a herbicide, more effective, or there may be a prolonging action. Such a prolonging action is particularly noted, as will be demonstrated, with certain combinations of melamine and herbicides.

Since the nitrogenous material has fertilizer value, contributing nitrogen values that become available over a long period of time following application, the amount of the nitrogenous compound that is applied may be adjusted to be quite large, to furnish a desired amount of fertilizing activity. However, for developing the property of prolonging the activity of the biologically active material, the ratio of the nitrogenous compound to the biologically active material should preferably be at least 3:1, in parts by weight. Generally, the ratio will be much higher than this, to take advantage of the fertilizing properties of the nitrogenous compound.

The prolonging and/or potentiating action of the nitrogenous compound, such as melamine, on the biologically active material, such as a herbicide, while perhaps being attributable to some kind of chemical reaction or hydrogen bonding, does not require any pre-reaction of these materials. Rather, the evidence indicates that when the materials are brought together in an aqueous medium, either in a liquid formulation or during the preparation of granules as will presently be described, the prolonging action may be observed after application. There is also some indication that the reaction, bonding, or combination of these can occur in the presence of soil moisture.

Generally the biologically active materials that are preferred for use in the invention are those herbicides that have chemical structures indicating that they would be suitable for hydrogen bonding with highly nitrogenous compounds such as the triazines, and particularly with melamine. Such compounds generally may be the highly halogenated compounds, carboxylic acids, hydroxy compounds, and the like.

The herbicides that are selected for use may be those that become effective through contact and, as well, those that are taken up from the soil. Suitable herbicides include defoliants, desiccants, eradicants, systemics and selective herbicides. The invention is useful for herbicides that are applied preplanting, after planting but pre-emergence, "cracking" types, which operate on the plants as they emerge from the soil, and post-emergent herbicides that are effective after there has been extensive emergence.

The liquid compositions of the invention may be applied in the form of bands, by broadcasting from large spray nozzles, through the use of a directed sprayer, and through the use of sprays or curtains of liquid that are applied over the top of crops, either by ground mobile equipment or by aerial application. The liquid compositions of the invention may include two or more herbicides in admixture, or in admixture with other materials such as liquid fertilizer materials. The liquid compositions may be incorporated into the top few inches of the soil, which is a procedure that tends to inhibit photodecomposition and/or volatilization. Moreover, mixing the liquid compositions into the top few inches of soil promotes activation of the active ingredients through normal soil moisture contents, if rain is insufficient. Ordinarily soil incorporation would be used with herbicides applied pre-planting. However, sequential, overlapping, and piggybacking applications may be made. For example, a pre-plant herbicide may be incorporated in the soil, followed up by a subsequent surface application of a suitable liquid composition.

Generally, those herbicides that are regarded as suitable include the amides, arsenicals, carbamates, thiocarbamates, carboxylic acids and their derivatives, dinitroanilines, heterocyclic N compounds, organophosphates, substituted ureas, quaternary N compounds, and inorganics.

The amide herbicides include a wide variety of chemical types, properties, types of applications, and crops upon which the herbicides are effective. Most of these are pre-emergent or pre-planting incorporated. They include Lasso ® and Dual ®. These materials may be in solid or liquid form.

The arsenicals include cacodylic acid and the salts of monomethyl- and dimethylarsinic acids. The arsenical herbicides based on cacodylic acid are defoliating or dessicating contact herbicides. The salts of the monomethylarsinic acids have lower contact toxicity and act through absorption.

The carbamates and thiocarbamates are generally applied to the soil and are taken up through the root systems. A few are foliar. Generally these compounds are volatile and when applied they are frequently incorporated in the top few inches of soil to retard volatilization. Herbicides of this type tend inhibit shoot growth in grasses. Commercial examples of herbicides of this type are sold under the trademarks Betanal ®, Betanex ®, Sutan ®, and Eptam ®.

Examples of carboxylic acid herbicides include phenoxy and benzoic acids, aliphatic acids, and carboxylic acids with heterocyclic rings. Generally, these molecules contain chlorine atoms, i.e., 2,4-D. They include herbicides that are applied to the soil, that act through foliar applications, that can be applied to grass, and that are effective against broad leaf weeds. Commercial herbicides of this kind are sold under the trademarks Banvel ® and Garlon ®.

Dinitroaniline herbicides are generally dinitrochlorobenzene reacted products. These tend to inhibit root growth and shoot growth. They are generally applied to the soil and exhibit low translocation. To control grass in soybeans and cotton, and weed germination, herbicides of this kind are generally incorporated in the soil. Commercial herbicides of this kind are sold under the trademarks Balan ® and Treflan ®.

Herbicides based on heterocyclic nitrogen compounds include the symmetrical triazine derivatives, pyridazones, and uracils. These are generally applied to the soil for pre-emergent control. They exhibit low to high translocation, depending on the particular herbicide. They are believed to be effective because of inhibition of oxygen production (the Hill reaction). Commercial examples are sold under the trademarks Aatrex ®, Basagran ®, Sencor ®, and Velpar ®.

While most of the organophosphates are best known as insecticides, and as such are considered to be potentially useful biologically active materials in liquid compositions of this invention, a few are active as plant growth regulators and herbicides. They have diverse structures and properties, and varied uses. Two commercial examples of herbicides are sold under the trademarks Bensulide ® and Betasan ®.

The urea herbicides generally are nonselective and usually are soil applied. There is rapid translocation. The herbicides are believed to be effective through inhibition of oxygen production (the Hill reaction). Commercial examples are sold under the trademarks Lorox ® and Tupersan ®.

The quaternary herbicides are usually considered to be contact foliars. Many of them are selective of annuals among perrenials. Some commercial products are sold under the trademarks Avenge ®, Diquat ® and Paraquat ®.

The inorganic herbicides generally are not selective. They have diverse chemistry and include such unrelated materials, for example, as sodium chlorate and sodium azide.

While herbicides are a preferred category of biologically active materials considered useful, the potentially useful materials also include a wide variety of insecticides. As available commercially, insecticides are generally available mixed with adjuvants, such as spreader-stickers; carriers such as a talc, bentonite, and diatomaceous earth; and neutralizers to overcome the catalytic action of some carriers, which tend to accelerate breakdown. Urea is sometimes used as a neutralizer.

For incorporation in a liquid composition of this invention, the insecticidal active ingredient must either go into solution or be capable of being placed in a suspension that is sufficiently stable to permit application at a reasonably uniform analysis. As purchased commercially, the insecticidal material that is to be used or evaluated may be a dry formulation in the form of a dust or dry powder, containing anywhere from 0.5% to 10% of the active ingredient. The insecticide may also be available in the form of granules. These tend to be larger particles than the dust or dry powders, and most often are made by spraying a solution or suspension of the active ingredient in a volatile solvent onto a pre-sized granular carrier. Generally sufficient active ingredient is applied so that the dried granules contain from 7% to 10% by weight of the active ingredient.

The insecticidal material may also be available in a liquid formulation, or in a wettable powder that is intended to be made up into a liquid formulation. The usual wettable powder contains from 25% to 75% by weight of active ingredient, mixed with a clay-like diluent or carrier, together with a wetting agent. Some insecticides are available as soluble powders and are miscible with water to rather high concentrations, on the order of 75% to 90% by weight.

Some of the insecticides that are expected to be useful in liquid compositions of the invention include chlorinated hydrocarbons, organic phosphates, carbamates, and synthetic pyrethroids.

The chlorinated hydrocarbon insecticides typically contain, in their molecules, hydrogen, carbon, and chlorine. Generally these act as stomach and contact poisons affecting the nervous system. They are persistent in the environment and tend to accumulate in animal fatty tissue. Examples are DDT and chlordane.

The organic phosphates generally are contact and/or stomach poisons. They are chemically unstable and so are less persistent in the environment than the chlorinated hydrocarbons. Generally they are metabolized readily in animals. They are considered highly toxic since they generally are cholinesterase inhibitors, interfering with nerve impulse transmission. Most of these materials are characterized by relatively low $LD_{50}$ values, although the value for malathion is 1400. Parathion is one of the best known organic phosphate insecticides and is considered to be an extremely dangerous material to handle. It is a systemic insecticide.

The carbamates generally are similar in action to the organic phosphate insecticides. They may be highly toxic but some of them are of very limited toxicity. Generally, these insecticides are not magnified in the food chain and are characterized by rather rapid breakdown, once applied.

The synthetic pyrethroids are commonly used in conjunction with other insecticides to provide quick knockdown. They react well with synergists and exhibit relatively low mammalian toxicity. Generally they breakdown quickly and leave little residue.

It appears that the principles of the invention are equally applicable to fungicides. There are several different classes of chemicals in common use against a variety of fungi.

The aniline/anilide fungicides are relatively few in number but important commercially. Botran ® and Dyrene ® are contact fungicides useful against foliar diseases. Vitavax ® fungicide is a systemic seed and soil treatment material useful for peanuts and loose smut on wheat.

The dithiocarbamate fungicides generally are protectants against diseases of apples, potatoes, and several vegetables. Products in this class include thiram, zineb, maneb, and Manzate ® 2000 fungicide.

The halogenated fungicides are used predominantly in connection with the peanuts, vegetables, and seed markets. Among the commercial products are Bravo ® chlorothalonil fungicide; Terrachlor ® fungicide, effective on contact; Terrazole ® fungicide, applied as a seed treatment for the control of pythium and phytophthora.

The heterocyclic nitrogen fungicides have protectant or systemic activity. They hold a major share in every market except potatoes and vegetables. Commercial products of this kind include the phthalamides such as Captan; Difolatan ® fungicide, useful as a protectant-contact fungicide; Benlate ® fungicide, which is widely used in connection with apples, peanuts and vegetables, and is a systemic fungicide; and Bayleton ® fungicide, which is often used on small grains to protect against rust.

In addition to these biocidal biologically active materials, there are a variety of other materials that can be expected to exhibit unusual undesirable properties when incorporated in liquid compositions according to the invention. Such materials would include Actidione antibiotic, many biologicals, and some metallics. Among the preferred biologically active materials for use in liquid compositions of the invention are those that are useful as pre-emergent or post-emergent herbicides, such as, for example, 2,4-D; trifluralin, which is trifluoro-2,6-dinitro-N,N-dipropyl-p-toluidine; DCPA, dimethyltetrachloroterephthalate; bensulide, [S-(O,O-diisopropylphosphorodithioate) ester of N-(2-mercaptoethyl) benzenesulfonamide; N-butyl-N-ethyl-$\alpha,\alpha,\alpha$-trifluoro-2,6-dinitro-p-toluidine; and atrazine and simazine.

While liquid formulations in accordance with the invention may be made up by combining in a liquid generally an aqueous vehicle, the selected biologically active material or materials and the selected nitrogenous compound or compounds, together with any other desired materials, it is also convenient to form some or all of the dry ingredients into granular form. The user can then place a quantity of the granules in the proper amount of water or aqueous solution, and stir, allowing time for the soluble binder to dissolve to release the slightly soluble fine particles of melamine or other selected nitrogenous compound. The formulation can then be applied as by spraying.

The dry ingredients can be granulated in a variety of ways, but the preferred processes for making such granular products are similar to those disclosed in copending application Ser. No. 305,603, filed Sept. 25, 1981, modified however to accomplish the incorporation in or on the granules of the biologically active substance. Some of the techniques for doing this are disclosed in copending application Ser. No. 518,281, filed July 28, 1983.

The latter application describes, as one embodiment of its disclosure, the formation of an intimate admixture of a biologically active material with at least as large, and preferably a larger, volume of particles of a nitrogenous material of the kind described in this present application, preferably melamine, made up in granular form with a soluble binder, preferably urea. In this form, the biologically active material is protected from the degradative effects of sunlight and oxygen, the leaching effect of water, the volatilization effects of wind and sun, as well as the microbiological breakdown initiated by microorganisms, following application of the granules to the soil.

In the present case, the granules are not intended to be added to the soil, but rather, to an aqueous vehicle to form a liquid formulation that may be applied to the soil or to foliage, for example.

In the embodiment of the present invention where some or all of the components of the sprayable composition are prepared in granular form, the processes used for making the granules are similar to those disclosed in copending application Ser. No. 305,603, filed Sept. 25, 1981, modified however if desired to accomplish the incorporation in or addition to the granules of the biologically active substance, which is generally a biocide, and preferably a herbicide, most preferably one that has selective toxicity for weeds.

It is possible to add the biologically active material to granules prepared in accordance with the disclosures of either of these two just-mentioned patent applications, by spraying a solution or suspension of the biologically active material on preformed granules. This places the biologically active material on the outer surface of the granules as a coating or layer.

A preferred technique for making the granules involves the incorporation of the biologically active material in the form of a powder with melamine or other like nitrogen compounds. This mixture is then continuously tumbled in a rotary drum in a fashion that is well known in the fertilizer art, while molten urea or the like is sprayed into the tumbling bed in the form of small droplets. As the tumbling continues, this technique forms granules from the mixture in the bed and the molten binder material. Granules formed in this way are characterized by high crush strengths. There are many possible variations to this technique, such as, for example, spraying a solution or suspension of the biologically active material on the tumbling bed of melamine particles, then spraying that tumbling bed with droplets of molten urea or other binder material. In another variation, the biologically active material can simply be sprayed on the surfaces of such preformed granules, to the desired concentration.

The composition of such granules comprises a mixture of: (a) the biologically active material; (b) one of the particulate sources of fertilizer nitrogen already described, that is characterized by a particle size of 10 mesh or less, preferably 40 mesh or less, and (c) a binder that holds the mixture in solid form. An inert or fertilizer filler may also be used. Moreover, since the intention is to add these granules to an aqueous vehicle, emulsifying, stabilizing and suspending material may also be incorporated in the granules. The granules generally may be from 1 mm. to 10 mm. in size for convenience in applying using ordinary mechanical handling and packaging of equipment of the type used for granular fertilizers.

The binder for holding the particles together in granular form should be readily soluble and preferably should have plant nutrient value. Thus the binder may be a readily soluble fertilizer material supplying nitrogen, such as urea, in a preferred embodiment. The granules must have strength, size and weight suitable for handling and storage, and preferably also for mechanical dispensing. The granules may be in the form of agglomerates, prills or flakes.

In a more specific embodiment, the granular composition comprises a mixture of: (a) a BAM having herbicidal properties; (b) particulate melamine having particle sizes predominantly less than 40 mesh (about 400 micrometers), and (c) a urea binder that holds the BAM, the melamine particles, and any other materials present, in granular form. This embodiment of the composition comprises: from about 1% or less up to about 30% by weight of the herbicidal material, and generally, not more than about 20%; from about 10% to about 95%, and more generally from 40% to 80%, by weight of particulate melamine; and from about 15% to about 90% and more generally from 20% to 60%, by weight of the urea binder.

Such granules then provide a convenient, readily handled and readily measurable means for adding the granulated ingredients to an aqueous vehicle to make up a liquid formulation that may be sprayable if desired.

The preferred high nitrogen material is particulate melamine. Experimental evidence demonstrates its efficacy with certain herbicides in making them more effective. It is believed that the nitrogen source may also be selected from the group consisting of melamine, benzoguanamine (2,4-diamino-6-phenyl-s-triazine), dicyandiamide, ammeline, ammelide, cyanuric acid, mixtures thereof, their inorganic salts, their organic salts, and mixtures thereof. These salts are preferably selected from the group consisting of the hydrochloride, hydroiodide, metaphosphate, nitrate, orthophosphate, orthophosphate dihydrate, pyrophosphate, potassium dihydrogen phosphate, bisulfate, and sulfite, and, as well, the cyanurate, chloroacetate, and formate salts, and mixtures thereof. All of these materials are characterized by poor or slight solubility in pH 7 water at 20° C., and by slow conversion in the soil to a form in which the nitrogen is useful to plant life growing in the soil. The useful salts also include those where the associated ions are substantially or entirely comprised of one or more of the nutrient elements recognized by the American Association of Plant Food Control Officials, such as N, P, K, S, Ca, Fe, Zn and B, among others, and represented by such compounds as melamine phosphate, nitrate, or sulfate; melamine borate; and ureidomelamine.

These nitrogen source materials, as ordinarily available commercially or as prepared, are in the form of very fine particles. In the case of melamine, for example, the commercially available product typically has crystalline particles that are smaller in size than 10 mesh, U.S. Standard Sieve size, that is, smaller than 2 mm. (2,000 micrometers), and almost all of which are smaller than about 40 mesh, that is, about 400 micrometers and less. Melamine as presently available commercially, from most sources, is a very fine, powdery, light material. For the purposes of the present invention, even extremely fine particles of melamine can be used. In some commercial processes for making melamine, extremely fine particles are removed from vent gas in a filter. Such fine particles have been utilized in preparing liquid compositions of the invention. Their large surface area can be expected to be advantageous upon application to the soil, for releasing plant nutrient nitrogen at a faster rate, and also for favoring hydrogen bonding and any chemical reactions that may occur. Hence, no lower limit on melamine particle size is specified. The same is true of the materials that may be used in place of melamine. Very fine particles are also useful in forming stable suspensions.

When the BAM is in powder form, preferably with particle sizes below 40 mesh, U.S. Standard Sieve, it may be mixed with dry crystals of or powdered melamine (or other similar nitrogen source), then granulated. When the BAM is a liquid, it may be sprayed on the melamine, or on a powdered binder material such as urea, or on both, then dried; or it may be mixed with a liquid binder component. It may also be sprayed directly on performed granules, which are then dried. It may also be first converted to powder form, then used. Or the BAM, if not in liquid form, in some cases may be converted to a solution or suspension, and used in whole or part as the binder for making granules.

In one preferred mode, to make granules, the particles of melamine or other similar slow release fertilizer material, and the particles of a BAM, preferably in admixture, are bound together in granular form with a soluble binder material. The binder may be selected from a broad spectrum of materials, but preferably is selected so that it is either inert, biodegradable, soil-conditioning, or preferably, has plant nutrient value.

Among the preferred binders are those selected from the group consisting of urea, readily soluble proteinaceous materials, readily soluble resins, and water-soluble latices of synthetic polymeric materials. Binders that have some plant nutrient value are most preferred, such as urea.

The binder that is used should produce a granule that is sufficiently strong, upon hardening or curing, to impart to the granule a crush strength of at least 450 g (1 lb), as determined by tests on ten granular agglomerates randomly selected, with sizes in the range from 3 mm to 4 mm, the results being averaged. Preferably, however, the crush strength is at least 900 g (2 lb), and more preferably, 1350 g (3 lb). A crush strength of about 450 g is comparable to conventional, commercial prilled urea and is adequate strength for use in most forms of commercial handling, storage, and packaging equipment. Higher crush strength values guard against breakage, as when the granules are bagged and the bags are stacked, and during handling.

When a readily soluble material such as urea or a salt, such as ammonium nitrate or potassium dihydrogen phosphate, is employed as the binder for the granules, the binder material will disintegrate rapidly in a liquid vehicle, and release the BAM and the slow release nitrogenous material, generally in the form of discrete particles of each, if that was their form when the granules were prepared.

Urea is the preferred binder, not only because it permits the production of granular products with sufficient crush strength, and having suitable weights, sizes and shapes for convenient use, but also because it is readily soluble and adds a valuable fast release nutrient material. When urea is used as a binder with fine particles of melamine, the urea will dissolve rapidly in water and release discrete particles of the melamine. Other readily soluble, fast release binders include ammonium sulfate, ammonium phosphate, diammonium phosphate, ammonium nitrate, potassium nitrate, potassium sulfate, potassium chloride, potassium dihydrogen phosphate, and ammonium chloride. Preferably such salts are used in combination with urea, a latex, or other binder that imparts greater strength. The granular products may additionally comprise other fertilizer materials such as potassium, phosphorus, and micronutrients. Examples of micronutrients include calcium, zinc, magnesium, iron, boron, cobalt, manganese, molybdenum and sodium.

The granular compositions that may be used in forming liquid, sprayable compositions of the present invention generally comprise an amount up to about 30% by weight of the BAM, preferably up to about 20%, and from about 10% to about 95% by weight of melamine or other slow release source of fertilizer nitrogen, preferably 10% to 85%; and more preferably up to about 10% by weight of BAM and from about 40% to about 80% by weight of the melamine, with a soluble binder. When the binder is urea, the amount used is from about 15% to 90% of the granule and preferably from about 15%, preferably 20%, to 60% of the granule. When the binder is soluble resin, less may often be used, i.e., about 5%–10%.

Since the granules are intended to be dispersed in an aqueous vehicle, they may be any convenient size. Preferably they have a size in the range of from about 1 mm to about 10 mm, and more preferably, up to about 5 mm, and most preferably, from 2 mm to 4 mm. Preferably, the granules in the 2 mm to 4 mm size range exhibit an average crush strength of at least 450 g (1 lb), and more preferably, at least 1350 g (3 lb).

In one method of making urea-melamine-BAM granules, particles of melamine and particles of the BAM are blended together with particles of urea. This blend is sprayed with water or with an aqueous solution of other material, in an agglomerating device such as a disc pelletizer or a rotating drum. The blend becomes tacky and agglomerates. The agglomerates are then dried in air by a conventional technique, as in a hot air over or fluidized bed, generally at a temperature below the melting point of the binder material.

Although granules are usually prepared by the techniques described above, they can be produced by extrusion, pressing and granulating, and briquetting.

If the granules contain all of the ingredients needed or desired in the liquid formulation, the granules are simply added to water and mixed. Depending upon the composition and concentration, the resulting mixture will be either a solution or a suspension of melamine particles in a solution. The ingredients employed can be selected to accomplish a particular desired result. However, there should always be present in the formulation the combination of melamine, either in solution, in suspension, or partly dissolved and partly suspended, with the biologically active material. Then, when the formulation is applied, upon drying there will be present, generally in intimate association, melamine together with biologically active material. It appears that this combination is responsible for the improved efficacy, such as the prolonged activity, that may be exhibited by the biologically active material, as compared to the case where the biologically active material is applied alone.

The melamine contributes slow release nitrogen fertilizer values. For best results with many crops, the slow release nitrogen should be complemented with fast release nitrogen. It is therefore preferred that urea be present in the sprayable formulation, or other fast release nitrogen source either alone or in combination with urea. Urea is a material of choice, however, since it is believed that the solubility of melamine in an aqueous vehicle is increased when dissolved urea is present in that vehicle.

To prevent or minimize settling of melamine particles or other particles, it is preferred that the aqueous sprayable formulation contain an additive or be mechanically agitated. The additive may be an emulsifying agent, a suspending agent, a stabilizing agent, or one or more agents that combine some of these properties. The presence of a wetting agent may be desirable, to improve the wetting characteristics of the sprayable formulation when applied to some substrates such as plant leaves. Other materials that may be incorporated in the liquid vehicle include one or more materials contributing soluble, fast release nitrogen values; potassium values; and phosphorus values.

Many herbicides and other pesticides are sold in the form of wettable powders. This physical form of the biologically active material is very convenient for incorporation in a granule, and also for incorporation in the liquid vehicle of a sprayable formulation. Some biologically active materials are also available in sprayable liquid form. Often, the most convenient and practical way to use such a sprayable biologically active material is by adding the other desired components to it, including more liquid if necessary for appropriate spraying consistency.

The invention will be demonstrated in several specific examples. These are intended to be illustrative only and are not intended to limit the invention. All parts and percentages are by weight, and all temperatures are Celsius, unless expressly stated to be otherwise.

EXAMPLE 1

A. Liquid Suspension 14-9-12 Fertilizer, Useful as a Liquid Vehicle

This example illustrates the preparation of a liquid suspension fertilizer formulation having a 14-9-12 analysis, that is useful as a liquid vehicle in making up a sprayable biocidal formulation. It was made up from several solid components that were formed into a suspension in water. One of these components was a batch of melamine-urea granules. The other dry components included monoammonium phosphate, clay, and potash. Another component was anhydrous ammonia.

Initially, a base composition, referred to as Base A, was made up by mixing together the following components:

| Base A | | |
|---|---|---|
| Component | Weight | % by Weight |
| Water | 165 lb | 30.75% |
| Monoammonium phosphate | 340 lb | 62.50% |
| Anhydrous ammonia | 30 lb | 5.25% |
| Clay | 10 lb | 1.50% |

The Base A composition prepared in this way amounted to 545 lb having the analysis 11-33-0. It was combined with other ingredients to make a liquid suspension fertilizer, as follows:

| Liquid Suspension Fertilizer | | |
|---|---|---|
| Component | Weight | % by Weight |
| Water | 675 lb | 33.75% |
| Base A | 545 lb | 27.25% |
| Melamine-urea granules (60-0-0) | 370 lb | 18.50% |
| Clay | 20 lb | 1.00% |
| 62% potash solution | 390 lb | 19.50% |
| Total | 2000 lb | 100.00% |

The melamine-urea granules were SUPER 60 fertilizer granules manufactured and sold by Melamine Chemicals, Inc. They were made up by mixing together approximately 70 parts by weight of melamine and 30 parts of pulverized urea powder, moistening, granulating, holding for an annealing period, and then permitting the granules to cool. The amount of nitrogen contributed by the melamine was about 45%, and the amount contributed by the urea was about 15%, for a total of about 60% nitrogen by weight of the granules.

B. Liquid Herbicidal-Fertilizer Formulations

A biologically active material can easily be incorporated into this balanced liquid fertilizer base by simple mixing.

The liquid suspension fertilizer is useful as a vehicle for oxadiazon 50WP, sold under the trademark Ronstar ® as a herbicide for pre-emergent grass control. Ordinarily this herbicide is recommended for application at 1 to 2 lb of the active ingredient per acre. When incorporated in the liquid suspension fertilizer above, application at the low end of the recommended range generally appears to be appropriate.

This exemplary liquid suspension fertilizer is also valuable for formulation with pre-post emergent wheat control agents. One such agent is chlorsulfuron, sold under the trademark Glean ® as a 75% DF. This is recommended for application at the rate of 0.2 to 0.5 oz of active ingredient per acre, for good post-emergent control of weeds. It also has some potential for pre-emergent control. When formulated with the above liquid fertilizer, superior efficacy can be expected.

The liquid suspension fertilizer is also a useful vehicle for the application of plant growth regulators. For example, Embark ® 2S mefluidide is easily mixed into the liquid suspension fertilizer. It can be applied at rates in the range of 0.125, or 0.25, or 0.375 lb of active ingredient per acre, depending upon the effect desired, with good efficacy when applied in the above liquid fertilizer.

In addition to the kinds of formulations suggested above, biologically active materials may be applied in combination. For example, combination of the post-emergent herbicides 2,4-D plus MCPP plus dicamba can be added to the liquid suspension fertilizer for use as a selective broad leaf weed control material, active through foliar uptake. Other combinations with similar activities are: 2,4-D plus 2,4-DP plus dicamba; triclopyr plus 2,4-D; and triclopyr plus chlorsulfuron. With these also, good prolongation of activity can be expected.

When the liquid suspension fertilizer described above is used as a BAM vehicle and applied at the rate of 500 lb of liquid suspension per acre, the rate of nitrogen application per acre is 70 lb. Of this 70 lb, 28.75 lb is readily soluble nitrogen from the MAP, anhydrous ammonia, and urea, and the remainder, 41.25 lb, is derived from the melamine and is released slowly.

EXAMPLE 2

Liquid Insecticidal Composition

Dursban ® insecticide, a product of Dow Chemical, is useful against chirch bugs, army worms, and bluegrass billbugs. It has residual activity of 7 through 14 days. It is usually applied at the rate of 1 lb of active ingredient per acre. Often it is applied with readily soluble fertilizer nitrogen at 1 lb of nitrogen per 1000 sq. ft. In a typical formulation, this amounts to 600 parts per million of Dursban ® insecticide, active ingredient, for each 3% of nitrogen in the sprayable solution.

Dursban ® insecticide is normally supplied as an emulsifiable liquid that contains 58% by weight of the active ingredient and 42% by weight of xylene. To use it in combination with melamine crystals, the desired amount of melamine is added together with a suitable suspending agent, such as, for example, about 0.1% by weight of the total formulation of Drew Chemicals SPD 12-674 dispersant. Preferably, however, a source of soluble nitrogen is also incorporated in the formulation.

When such a formulation is applied to turf grass, for example, the efficacy of the insecticide can be expected to be improved compared to that normally observed in the absence of melamine.

When this kind of formulation or a similar formulation is applied to grass, drops ordinarily are deposited on the blades of grass. Each drop contains very small quantities of dissolved melamine, and some suspended melamine, and either suspended and/or dissolved biologically active material, in this case, Dursban insecticide. As the drop dries and the liquid evaporates, the surface tension forces will tend to pull together and concentrate the melamine and the insecticide. The dissolved melamine will begin to crystallize out and to bind any pre-existing particles already present together. It is theorized that this creates the equivalent of a small granule on the surface of the blade of grass, or on the soil, wherever the drying occurs. Thus, the physical protection afforded by the melamine is believed to supplement the action of any hydrogen bonding or chemical reaction that may take place or may have taken place between the melamine or other nitrogen source, and the biologically active material.

EXAMPLE 3

Sprayable Herbicidal Formulation

Balan ® herbicide is sold as a wettable powder. It is ordinarily applied at the rate of 2 lb per acre of active ingredient in a formulation that furnishes 40 lb of nitrogen per acre.

A sprayable Balan ® herbicide formulation is made up using 174 gallons of water for each acre to which the formulation is to be applied. Two lb of the commercial Balan ® wettable powder is added to each 174 gallons of water, together with 30 lb of fine particles of commercially available melamine having a particle size of 400 micrometers or less, predominantly. This amount of melamine supplies 20 lb of nitrogen.

To make up the nitrogen content to the desired level of 40 lb per acre, urea is added. The requisite amount of 42.9 lb of urea dissolves readily in the water.

Ordinarily, 174 gallons of water would dissolve about 7 lb of melamine. Since melamine is somewhat more soluble in a urea solution than in plain water, more melamine may actually dissolve than 7 lb, depending on temperature, the presence of other dissolved substances, and like factors. However, whatever amount of melamine remains undissolved becomes suspended in the liquid vehicle so that the final formulation becomes a suspension in a solution. The stability of the suspension is good even with very little agitation, because of the very small size of the melamine particles. However, the presence of a suspending agent, or thickener, is useful in further stabilization and in the prevention of settling.

When this formulation is applied by spraying, each individual drop will contain some particles of the Balan ® herbicide, usually some particles of suspended melamine, and the liquid portion will contain dissolved melamine. There may also be other chemicals present in each drop, such as urea. As the individual droplet dries and the water present evaporates, the surface tension forces within the drop will pull together the suspended particles of the Balan ® herbicide and the suspended melamine particles. The dissolved melamine particles also begin to crystallize out, and to bond the already present particles together. This action creates the equivalent of a very small granule on the surface on which the drop has been applied and on which it dries. The presence together of the melamine and the Balan ® herbicide is believed to be responsible for the extended activity that can be expected to be observed for the herbicide.

This type of herbicidal suspension is useful for application to turf grass for the control of crabgrass.

In similar fashion, sprayable herbicidal compositions can be made up containing other herbicidal materials. For example, Betasan ® brand of bensulide, (Stauffer Chemical Corp.), provides broad spectrum control of weeds. It has selected agricultural applications on some vegetables such as carrots. The half-life is quite long, and the solubility is low, 20 ppm. Betasan ® herbicide may be prepared into sprayable herbicidal suspensions in the manner described in this example, using the appropriate amount of active ingredient per acre for making up the formulation. Generally the application rates are higher in the south than in the north for this particular herbicide, and multiple repeated small applications are more effective than one larger application. It is believed that use of the present invention will eliminate the need for multiple applications or make fewer applications possible, by prolonging activity substantially.

Atrazine is a herbicide product of Ciba-Geigy [2-chloro-4-(ethylamino)-6-(isopropylamino)-s-triazine], which is useful on Saint Augustine grass and other warm season grasses during the fall-winter grass dormancy. It can be made up into sprayable suspensions in the manner described above, the appropriate application rate being about 1 lb to a maximum of 2 lb of active ingredient per acre.

EXAMPLE 4

Liquid Herbicides for Douglas-Fir Seedlings

Granules containing herbicidal material were made up in accordance with the following formulations:

(a) 2,4-D 5%, melamine 71%, urea 24%;

(b) 2,4-D/KL (a controlled release formulation of 2,4-D with kraft lignin) 10%, melamine 72%, urea 18%.

To make up liquid herbicidal formulations, the granules (a) and (b) are each placed in appropriate quantities of water, with mixing. In addition, as a comparison control, 2,4-D in liquid form is made up for application at a conventional commercial rate.

To evaluate these formulations, Douglas-fir seedlings (2.0) are planted in 10" diameter pots. The several treatments involved are each applied to three potted firs. One set of potted seedlings is selected as a control to receive no treatment whatever. A second set of potted seedlings is selected to receive a commercial rate application of the liquid form of 2,4-D made up as the comparison control. In this and in all other cases in this example where 2,4-D is applied, it is applied at a rate equivalent to 20 lb of active ingredient per acre. Liquid formulations made up from granule lots (a) and (b) are also applied, each to a different set of potted seedlings.

These sets are then monitored for seedling height growth, growth quality of the seedling, and weed growth surrounding the seedling represented as a percentage of soil surface. Initially, there should be no visible weeds present on the soil at the time of treatment. However, since volunteer weed seeds are always present in the atmosphere as well as in the soil, they daily settle on the surface of the soil in the pots, and all pots are exposed in essentially the same way.

The control plantings with no treatment generally are overrun with weeds in about 8 weeks, over 100% of the soil surface, with the weeds surrounding and overtowering the seedlings. Normally all other treatments will exhibit better mean height growth.

The commercial rate 2,4-D application initially will give good weed control, but since 2,4-D has a short period of activity, as soon as its effectiveness diminishes, weeds invade. After 14 weeks, the weed population can be expected to occupy about 90% of the soil surface. Nevertheless, mean height growth can be expected to be substantially better than that observed in the case of the no treatment control seedlings, by a substantial percentage.

Both liquid formulations made up from the melamine granules can be expected to give good, long lasting weed control, lasting up to 24 weeks. The corresponding growth of the seedlings should be excellent, and at the end of this period, there should be a second bud flush. Mean growth can be expected to be at least 75% better than that of the no treatment control seedlings, at least in part as a result of much reduced weed competition.

In place of the 2,4-D herbicide in either form, other herbicides can be used. For Douglas-fir seedlings, Velpar ® herbicide is also favored.

Hexazinone herbicide is a du Pont product believed to contain about 90% by weight of the active ingredient hexazinone (3-cyclohexyl-6-(dimethylamino)-1-methyl-1,3,5-triazine-2,4(1H,3-H)-dione) plus 10% inert ingredients. Hexazinone is availabe commercially in both a solid and liquid form. The liquid form is available under the traedemark Velpar ® L, containing about 4 lb of active ingredient per gallon. The liquid form is usually formulated into a sprayable composition. In the solid form, the hexazinone is granular and contains from 5% to 10% by weight of the active ingredient on an inert clay substrate, available under the trademark Pronone 5G or 10G. It is believed that moisture is required to activate hexazinone in the soil.

When melamine-urea granules are prepared containing about 0.5% to 1.5% by weight of the active ingredient of Velpar ® hexazinone herbicide, and the granules are then made up into a liquid formulation, excellent long term weed control, with accompanying good growth benefits on the part of the seedlings, can be expected. An alternative way to make up such a sprayable formulation is to add melamine/urea granules to a formulation of Velpar ® L herbicide in an aqueous vehicle. The granules can be made up with a combination of more than one herbicide, for example, the combination of both 2,4-D and Velpar ® herbicide. Such a combination can be dissolved in an aqueous vehicle to form a liquid herbicidal formulation.

In using these herbicidal formulations, it is preferred that the liquid be applied as a spray directly to the earth, and that a heavy spray be used to minimize and preferably to eliminate drift. For aerial application, timing of the application is important, since growth from buds is sensitive.

EXAMPLE 5

Liquid Herbicidal Formulations From Granules Having a Urea Binder

Several granule formulations were prepared using melamine particles, powdered urea, and a BAM, in the form of a finely divided powder. The granules were prepared by mixing the dry ingredients, tumbling, spraying to moisten the urea and make it tacky, and drying. Representative granule formulations included the following, where all parts and percentages are by weight, dry basis, unless otherwise indicated.

| A. Herbicide Formulations - Urea Binder | | |
|---|---|---|
| 5A1 | Melamine | 78 g |
| | Urea | 20 g |
| | 2,4-dichlorophenoxybutyric acid (2,4-DB) | 2 g |
| 5A2 | Melamine | 78 g |
| | Urea | 20 g |
| | Treflan ® brand of trifluralin (α,α,α-trifluoro-2,6-dinitro-N,N-dipropyl-p-toluidine) | 2 g |
| 5A3 | Melamine | 78 g |
| | Urea | 20 g |
| | Dicamba (3,6-dichloro-o-anisic acid) | 2 g |
| 5A4 | Melamine | 63.3 pts. |
| | Urea | 31.6 pts |
| | Cotoran ® brand of fluometuron (1,1-dimethyl-3-(α,α,α-trifluoro-m-tolyl)urea) (80 wt. %) | 4 pts. (as received) |
| 5A5 | Melamine | 63.3 pts |
| | Urea | 31.6 pts. |
| | Dacthal ® brand of DCPA (dimethyl tetrachloroterephthalate) (75 wt. %) | 20 pts. (as received) |
| 5A6 | Melamine | 63.3 pts. |
| | Urea | 31.6 pts |
| | Lorox ® brand of linuron (3-(3,4-dichlorophenyl)-1-methoxy-1-methylurea); or, (N'-(3,4-dichlorophenyl)-N-methoxy-N-methylurea)) (50 wt. %) | 5 pts. (as received) |
| 5A7 | Melamine | 63.3 pts. |
| | Urea | 31.6 pts. |
| | Prowl ® brand of N-(1-ethylpropyl)-2,6-dinitro-3,4-xylidine) about 1.68 pts. active ingredient) | 5.1 pts. (as received) |
| 5A8 | Melamine | 63.3 pts. |
| | Urea | 31.6 pts. |
| | Basalin ® brand of N-(2-chloroethyl)-α,α,α-trifluoro-2,6-dinitro-N-propyl-p toluidine (4 lb/gallon) (about 2.44 pts. active ingredient) | 5.1 pts. (as received) |
| 5A9 | Melamine | 64 pts. |
| | Urea | 32 pts. |
| | Ronstar ® brand of | 8 pts. (as |

A. Herbicide Formulations - Urea Binder

| | |
|---|---|
| oxadiazon (2-tert-butyl-4-(2,4-dichloro-5-isopropoxyphenyl)-$\Delta^2$-1,3,4-oxadiazolin-5-one) | received) |
| 5A10 Melamine | 64 pts. |
| Urea | 32 pts. |
| Dual ® brand of | 4 pts. (as received) |
| metolachlor (2-chloro-6'-ethyl-N-(2-methyl-1-methylethyl)acet-o-toluidide) | |
| 5A11 Melamine | 63.3 pts. |
| Urea | 31.6 pts. |
| Aatrex ® brand of | 5 pts. (as received) |
| atrazine(2-chloro-4(ethylamino)-6-(isopropylamino)-s-triazine) (80 wt. %) | |
| 5A12 Melamine | 63.3 pts. |
| Urea | 31.6 pts. |
| Bladex ® brand of | 5 pts. (as received) |
| cyanazine (2-[[4-chloro-6-(ethylamino)-s-triazin-2-yl]amino]-2-methylpropionitrile) (80 wt. %) | |
| 5A13 Melamine | 63.3 pts. |
| Urea | 31.6 pts. |
| Propham (isopropyl carbanilate) | 6 pts. |

Each of these granular formulations is easily made up into a sprayable liquid formulation upon addition of the appropriate amount of water and stirring until all of the granules have disintegrated and all of the released material is distributed uniformly. The suspended solids are very fine and are readily sprayable.

In each case, the applied sprayable formulation, upon drying, can be expected to exhibit improved efficacy; in many cases, exhibiting activity substantially greater than that of the herbicide if applied alone or in a conventional commercial formulation.

EXAMPLE 6

Sprayable Growth Regulating Formulations

Granules were prepared following the same techniques as in the preceding example, but using a growth retardant material as the biologically active material, as follows:

| | | |
|---|---|---|
| 6A1 | Melamine | 63.3 pts. |
| | Urea | 31.6 pts. |
| | Maleic Hydrazide | 6 pts. |
| 6A2 | Melamine | 63.3 pts. |
| | Urea | 31.6 pts. |
| | Alar ® brand of daminozide(N,N-dimethylsuccinamic acid) | 6 pts. |

When batches of these granules respectively are placed in the appropriate quantity of water, permitted to disintegrate, and then stirred to insure uniformity, a sprayable growth retardant formulation is obtained. It can be applied in the usual fashion, by spraying directly on the plant life that is to be affected. A substantial prolongation of activity can be expected as compared to application of the growth retardant in the conventional way.

EXAMPLE 7

Sprayable Herbicidal Compositions for Use on Soybeans

A. Lasso ® Herbicide

The herbicide employed was commercially available Lasso ® alachlor herbicide, which is a liquid form of the herbicide containing 45.1% active ingredient per gallon.

Two batches of granules were made up with different contents of herbicide, one being twice as strong as the other in terms of weight of active ingredient used.

In both cases, the production process was the same. Melamine and urea were mixed with the liquid herbicide, and enough moisture was added to permit granulation. The two batches of dried granules have the following respective compositions:

| | Batch 7-A-1 | Batch 7-A-2 |
|---|---|---|
| Wt. % Lasso ® liquid (as is) in the granules | 2.96 | 4.83 |
| Melamine % | 40.76 | 39.97 |
| Urea % | 56.28 | 55.20 |
| Total | 100.00 | 100.00 |

Batch 7-A-1 contains about 53% nitrogen, whereas Batch 7-A-2 contains about 52% nitrogen. These batches of granules can be dissolved, respectively, in enough water for convenient application at the rate of 1.5 lb of active ingredient per acre, and 2.5 lb of active ingredient per acre, respectively. Batch 7-A-1 contains 1.335% active ingredient in the granules, and Batch 7-A-2 contains 2.178% active ingredient in the granules.

The ratio of melamine to active ingredient in the two batches is, respectively, 30:1 and 18:1, dry basis.

When sprayed in the manner recommended for this herbicide, improved efficacy should be observed, because of the presence and intimate association of the melamine particles with herbicide particles.

B. Lorox ® Herbicide

Chemically, the active ingredient of this herbicide is 3-(3,4-dichlorophenyl)-1-methoxy-1-methylurea. When used as recommended by the manufacturer, linuron herbicide selectively controls germinating and newly established broad leaf weeds and grasses in crops such as soybeans, cotton, corn, sorghum, potatoes, carrots, and parsnips. It is generally sprayed on the soil as a pre-emergence or post-emergence treatment, often in a spray formulation with a suitable surfactant.

As in Example 7A, granules were prepared. However, Lorox ® linuron herbicide is a powder containing 50% of the active ingredient. Accordingly, it was mixed with melamine and urea, and the mixture was wetted with water for granulating purposes.

As in the example reported immediately above, two batches of granules were prepared, one at twice the strength of the other, as follows:

| | Batch 7-B-1 | Batch 7-B-2 |
|---|---|---|
| Wt. % Lorox ® powder as is in the granules | 0.91 | 1.80 |
| Melamine % | 41.62 | 41.24 |
| Urea % | 57.47 | 56.96 |

|  | Batch 7-B-1 | Batch 7-B-2 |
|---|---|---|
| Total | 100.00 | 100.00 |

For application, each batch is made up of the appropriate quantity of water for the application, respectively, of 0.5 lb of active ingredient per acre, and 1.0 lb of active ingredient per acre, respectively. The melamine/herbicide ratio, by weight, is 90:1 and 45:1, respectively, dry basis.

When sprayed in the manner recommended for this herbicide, improved efficacy should be observed, because of the presence and intimate association of the melamine particles with herbicide particles.

EXAMPLE 8

Liquid Formulations for Nutrition and Growth Regulation

A base for a simple liquid formulation is prepared with the following composition:

| Base Formulation | |
|---|---|
| Ingredient | % by Weight |
| Melamine | 70.0 |
| Water | 29.9 |
| Drew SPD12-674 dispersing agent | 0.1 |
| Total | 100.00 |

This base composition is a thick slurry of fine particles of melamine. It is useful in formulating plant growth regulating liquid formulations. Such compositions can be made up, for example, by adding appropriate amounts of a desired plant growth regulator to the base composition. Then, for spray application, for every one part of the base composition, from 3 to 5 parts of water are added, depending upon the desired concentration of the active ingredient.

Such a sprayable formulation provides both nutrition and growth regulation. The quantity and quality of nutrition can, of course, be easily adjusted by adding other fertilizer components to the liquid vehicle of the suspension.

Similar base composition formulations are described below:

| | Base Composition Formulations | | | |
|---|---|---|---|---|
| | Amount in Parts by Weight of the Base Composition | | | |
| Component | 8-2 | 8-3 | 8-4 | 8-5 |
| Nitrogenous component: | | | | |
| melamine | 454 | 454 | | 9.08* |
| ammeline | | | 200 | |
| Suspending agent: | | | | |
| Min-U-Gel 200 | 454 | | | |
| Min-U-Gel FG | | 454 | 200 | |
| Water | 3632 | 3632 | 1600 | 3632 |

*The melamine particles used in this demonstration of the invention were very fine, as evidenced by recovery from a filter. The % retained was approximately: up to 5% on 100 mesh; 30% on 325 mesh; and through 325 mesh, approximately 65%.

Such base compositions are easily modified to include other fertilizer nutrients as well as biologically active materials. The triazine component can be expected to potentiate the biologically active material to make it more efficacious.

A somewhat similar formulation for a base composition, using different ingredients, can be made up in the following manner. A reactor tank is charged with 56.1 lb of water. Then 1.5 lb of a Drew Chemical Co. dispersant, SPD12-674, is added to the reactor, along with 5.0 lb of a Drew Chemical Co. silicone defoamer (stabilizer), SPD12-723. These materials are warmed and agitated until both the dispersant and the defoamer have dissolved.

At that time, 37.4 lb of MCI ® urea/melamine granules, assaying 55% nitrogen, are added. These granules contain 42% by weight melamine approximately, the balance being the urea binder. The reactor is then stirred until the granules disintegrate. The urea binder dissolves in the water, and the melamine particles are dispersed in the water, forming a suspension of fine melamine particles. Since melamine is soluble in water and more soluble in urea solutions, some of the melamine goes into solution so that the liquid vehicle, so far as the melamine is concerned, is a combined solution/suspension.

To make this just-described base formulation into an effective liquid herbicidal composition, an appropriate amount of Lasso ® liquid alachlor herbicide, containing 45.1% by weight of active ingredient is added and mixed in. If the alachlor concentration suggested on the label is to be used, then the amount of liquid Lasso alachlor added is 2.28 lb Because of the potentiating effect of the melamine, for many applications, only 1.14 lb would be added. Since the amount of liquid base formulation made up was 100.0 lb, the concentration of the alachlor is easily calculated.

The same base formulation may conveniently be used to make up a liquid herbicide using Lorox ® linuron herbicide powder containing 50% by weight active ingredient. For making up a liquid herbicidal composition having the active ingredient at the concentration recommended on the label, 0.68 lb of Lorox powder are added to 100 lb of the base formulation. Because of the potentiating effect of the melamine, for some applications it may be desirable to add only one-half that amount of Lorox powder, that is, 0.34 lb per 100 lb of the base formulation.

EXAMPLE 9

Field Study, Melamine-Hexazinone Reforestation Experiments

This demonstration of the invention was conducted to establish the effect on herbicidal activity attributable to the presence of melamine crystals, where the herbicide formulation was applied to newly-planted conifers. Two different rates of nitrogen application were employed. Several different application techniques were used to determine any possible effect exerted by the application technique employed.

Study Conditions

The study was established in three locations to provide an array of environmental conditions.

The Valley Site (3½ miles south of Philomath, Oreg.) is on a Christmas tree operation owned by Holiday Tree Farms. It is a heavy Bellpine of Jory soil, southerly 10% slope, with a 12 year history of Christmas tree production. During this 12 year period, an estimated 40 lb/acre/yr of nitrogen have been removed during harvest, with no nitrogen additions. Lime, K₂O and P₂O₅ were added before the first crop was planted; the second crop, all Douglas-fir, was just harvested. A light stand of bentgrass (*Agrostis tenuis*) and scattered trailing blackberry (*Rubus ursinus*) are the prevailing cover. During the past 12 years, annual weed control has been maintained at a bare-soil level. Precipitation is about 50"/year, of which 87% occurs between October 1 and March 31.

The Five River site is on Newton Forests property about 35 miles west of the Valley Site, in a coastal valley of the Coast Range. The land is a highly productive site that has been used for grain crops and pasturage. Soils are alluvial fine sandy loams to sandy loams with gradients less than 5 percent. Historically it has had exploitive treatment with low or negligible fertilization. Rainfall is 90–100 inches per year. Current cover consists of a heavy stand of bentgrass, intermingled with velvetgrass (*Holcut lanatus*), tansy ragwort (*Senecis jacobea*), several legumes, of which vetches (Vicia sp) are prominent and scattered bracken (*Pteridium aguilinum*). 7-year-old Douglas-fir is planted in the area, with rows on a 16-foot spacing, permitting plots between rows.

The Camas Valley Site is about 30 miles southwest of Roseburg in a relatively dry section of the Oregon Coast Range. The site is like the Valley Site, a clay loam soil, nearly flat, that has been used for Christmas trees for 13–14 years on the Wayman Schmidt property. In the history of the plantation, two crops of Douglas-fir have been removed, with a depletion of some 520 lb/acre of nitrogen, of which less than 200 lb/acre have been restored by fertilization. Plant cover includes much catsear (*Hypochaeris radicata*) and St. Johnswort with scattered bentgrass, ryegrass and trailing blackberry. The site has had annual applications of herbicides to remove herbs, and the community present is considered moderately resistant.

Treatment

The study was designed as a complete block factorial, with three levels of N, (0, 100 lb, 200 lb), and four levels of hexazinone (0, ½ lb, and 2 lb/acre). The complete study was repeated 3 times, twice with hexazinone and N applied separately (once with N from 55% N melamine-urea granules, once from urea), and once where hexazinone was combined in 55% N melamine-urea granules. In addition, a partial series was established in which hexazinone/55% N melamine-urea granules were dispersed in 200 gallons of water, and applied as a slurry at the rate of 200 lb/acre N plus the four different rates of hexazinone.

Plot size was 10'×43' on Valley and Five Rivers Sites and 10'×50' at Camas Valley to accommodate tree spacing needs. Each plot was planted with at least ten each of 2-0 bare-root Douglas-fir and noble fir seedlings at approximately 5-foot spacing.

Treatments were randomized among 62 plot blanks at each site so that 31 plots were selected for the initial hexazinone treatments. Control plots were in triplicate on each site, and 28 plots were treated.

Trees were hand planted during the third week of March, 1984. The Valley plots were treated March 28, Camas Valley March 30, and Five Rivers Apr. 6, 1984.

In the first treatment, liquid hexazinone was applied with a hand-held boom fed by a pressurized sprayer system. It was noted at the end of the Five Rivers treatment that the regulator had malfunctioned to an unknown degree, causing a minor reduction in dosage on that site. In other treatments, prill fertilizer/hexazinone materials were applied with a hand-held rotary dispenser operated so as to provide a 10' swath. No problems were encountered.

The liquid, high volume slurry was applied with a solo backpack sprayer equipped with a Cooper-Pegler wand with an in-line filter of about 30 mesh. Many passes were required to disperse the two gallons of liquid on the 1/100 acre plots, using a downward-directed nozzle, waved back and forth with the "waving wand" technique. Although distribution was undoubtedly good with this technique, the volume of 200 gallons per acre was clearly excessive for operational use, and the solubility of the granules was inadequate to put into solution/slurry that would not plug the screen in the line. The material appearing on the screen had the character of hexazinone 90 percent dry product that salt out of cooling water, as if the highly soluble urea caused some precipitation. Despite this, there is no evidence that this created deposit anomalies.

SUMMARY OF TESTING

TABLE 8-1

| | | Percent Bare Ground, Average Three Sites[1] | | | |
|---|---|---|---|---|---|
| | | Hexazinone Rates; lb active | N application, lb/acre | | |
| No. | Treatments | ingredient/acre | 0 | 100 | 200 |
| 1 | Velpar ® L[2] liquid spray, | ½ | 10 | 3 | 0 |
| | plus Urea prills | 1 | 35 | 12 | 7 |
| | separately applied | 2 | 42 | 47 | 45 |
| 2 | Velpar ® liquid spray, | ½ | | 0 | 2 |
| | plus MCI 55[3] % N granules | 1 | | 20 | 17 |
| | separately applied | 2 | | 45 | 43 |
| 3 | Hexazinone incorporated | ½ | | 10 | 38 |
| | at 1.1% into the | 1 | | 46 | 57 |
| | MCI 55% N by weight granule | 2 | | 81 | 78 |
| 4 | Velpar ® L spray with | ½ | | | 45 |
| | MCI 55% N granules dispersed[4] | 1 | | | 60 |
| | into the liquid | 2 | | | 70 |
| 5 | Controls (no hexazinone) | | | | |
| | a. Urea prills 200 lb N/acre. | 0 | 9 | 0 | 3 |
| | b. MCI 55% N granules | 0 | — | 5 | 23 |

TABLE 8-1-continued

| | | Percent Bare Ground, Average Three Sites[1] | | |
|---|---|---|---|---|
| | | Hexazinone Rates; lb active | N application, lb/acre | |
| No. | Treatments | ingredient/acre | 0 | 100 | 200 |
| | 200 lb N/acre | | | | |

[1]Five Rivers (wet site); Camas Valley (dry site); Philomath (valley site).
[2]Velpar ® L liquid has about 2 lb hexazinone active ingredient per gallon.
[3]MCI ® 55% N granules are 55% Total N comprised of 27.5% N from urea and 27.5% N from the triamino-s-triazine.
[4]When the MCI 55% N granules are dispersed into the Velpar ® L spray liquid mix the urea component dissolves into solution while the melamine component remains essentially undissolved as a suspended powder.

As footnote 3 in connection with Table 8-1 indicates, of the total amount of nitrogen applied, half is from the readily soluble urea and half from the poorly soluble melamine. The readings on bare ground in Table 8-1, and on weed vigor reported below in Table 8-2, were taken about 6 weeks from the treatment date. At that time, the amount of nitrogen available from the melamine would have been essentially negligible, whereas substantially all of the nitrogen from the urea would have been available, subject to such factors as rainfall, translocation, and the like.

In analyzing the data in Table 8-1, the values reported for hexazinone applied at 2 lb per acre and for nitrogen applied to a total of 200 lb per acre are believed to be significant. In analyzing the data, it is noted that the fast release nitrogen from the urea tends to stimulate plant growth and vigor. The hexazinone, on the contrary, tends to limit plant growth and destroy plant vigor. Thus, the results for plot group 3, where the hexazinone was incorporated in the granules, and for plot group 4, where hexazinone and melamine particles were sprayed simultaneously in a single liquid vehicle, appear to be significant by comparison with the values that are comparable for plot group Nos. 1 and 2. At these levels of hexazinone and melamine, as reported in the results for plot group Nos. 3 and 4, there appears to have been significant co-action. The herbicide appears to have been potentiated and its efficacy increased, by co-application of the hexazinone herbicide with melamine particles, whether in granule form or in a common liquid vehicle.

In Table 8-2 below, a summary report is presented of average wheat vigor. The raw data from which this table was prepared includes observations made when no herbicide was applied, and nitrogen application rates of 0, 100, and 200 lb N per acre. In assembling the raw data, the observations were made following the common practice in this art. Grass vigor was compared to a control. A positive reading meant that the herbaceous material was more vigorous than the control. A negative reading indicated that the herbaceous material was more chlorotic than the control in appearance. The rating values fell in the range from −3 to +3, including 0, as is conventional.

For the purposes of 8-2, and to make the results more easily understood without a great deal of study, the raw data has been condensed. A single − sign for vigor rating means that generally the observations made (reported in Table 8-2 for 200 lb N/acre) were positive, in the range from 0 to +2. Where two + + appear, the rating was above +2. A single negative sign in Table 8-2 means that generally the reported values were in the range from 0 to −2.

The reported values of weed vigor in Table 8-2 demonstrate that a combined liquid application of hexazinone and melamine resulted in much less weed vigor than the cases where the hexazinone was incorporated in melamine/urea granules, or where the hexazinone was applied separately from either urea prills or melamine/urea granules.

TABLE 8-2

| | | Weed Vigor[1] Average Three Sites | |
|---|---|---|---|
| Plot Group No. | Treatments | Hexazinone Rates; lb/acre | Vigor Rating[2]; N applied at 200 lb/acre |
| 1 | Velpar ® L liquid spray, plus Urea prills separately applied | ½ 1 2 | + + <br> + + <br> + |
| 2 | Velpar ® L liquid spray, plus MCI 55% N granules separately applied | ½ 1 2 | + <br> + <br> + |
| 3 | Hexazinone incorporated at 1.1% by weight into the MCI 55% N granule | ½ 1 2 | 0 <br> 0 <br> − |
| 4 | Velpar ® L liquid spray with MCI 55% N granules dispersed into the liquid | ½ 1 2 | − <br> − <br> − |

[1]Vigor is degree of green color and apparent health of grasses and herbaceous vegetation remaining on the treatment plots.
[2]Rating compares vigor of the weeds in the treatment plots with a control treatment of no application of hexazinone or nitrogen which was assigned a zero rating. A (+) rating is more vigorous than the control and a (−) rating less vigorous.

The studies in Tables 8-1 appear to indicate that the combined application of hexazinone with urea and melamine, whether in the form of granules or in the form of a liquid slurry, is more effective for weed kill or inhibition, and for reducing the vigor of weeds that are present, than comparable applications of hexazinone in the form of a liquid spray combined with the separate application of urea prills, or the separate application of hexazinone in a liquid spray plus the separate application of urea-melamine granules containing 55% nitrogen. This increase in effectiveness of weed kill or inhibition is believed to be attributable to the coaction that apparently is observed when melamine and hexazinone are applied together in such form as to permit co-action.

The data reported in the two tables above demonstrate that when there is co-application of melamine with hexazinone herbicide, there is earlier activity and the herbicide is more efficient. Other data, not reported above, indicated a prolongation of activity as measured against grass germination.

CONCLUSION

There appears to be a definite improvement in efficacy when a herbicidal biologically active material is applied to plant life or to the soil, in either granular or slurry/solution association with one of the enumerated nitrogenous materials, and particularly, with melamine.

This invention is particularly useful for aerial application of a slurry/solution to a stand of trees or seedlings. If so used, it should be applied prior to bud break in the spring. While the improvement mechanism is not fully understood, it is speculated that hydrogen bonding is involved, and that accordingly, those biologically active materials that are susceptible to hydrogen bonding with the nitrogenous material, such as melamine, are particularly useful.

It is also possible that the mechanism responsible for improved results has little to do with either hydrogen bonding or chemical reactivity, but rather depends upon some physiological factors. Thus the triazine, such as melamine, may stimulate some sort of response in the plant to make it more susceptible to the action of the herbicide. At present, the available evidence appears to favor hydrogen bonding or chemical reaction, since an essentially simultaneous but separate application of the materials is not as effective as co-application either in granular or liquid forms.

While the sprayable liquid formulations can be made up in many different ways, one preferred way is by first incorporating the biologically active material in melamine/urea granules, then placing a quantity of the granules in water and agitating. The proportions can be adjusted to suit the particular application and rate of application. Generally, however, the weight ratio of melamine to herbicide, or other nitrogenous compound to biologically active material, is preferred to be at least 3:1, as a matter of empirical observation. Other desired components in the sprayable liquid formulation may be incorporated in the granules, or may be added to the liquid vehicle. Incorporation of all or at least a substantial part of the solid components in granules facilitates shipping and measurements, and offers convenience while at the same time decreasing the risk of human error in formulating.

Among those herbicides that are preferred for use by incorporation in melamine/urea granules, for subsequent mixing with water to make a sprayable liquid formulation, the following are mentioned: trifluralin, $\alpha,\alpha,\alpha$-trifluoro-2,6-dinitro-N,N-dipropyl-p-toluidine; dicamba, 3,6-dichloro-o-anisic acid; fluometuron, 1,1-dimethyl-3-($\alpha,\alpha,\alpha$-trifluoro-m-tolyl)urea; fluorodifen, p-nitrophenyl $\alpha,\alpha,\alpha$-trifluoro-2-nitro-p-tolyl ether; linuron, 3-(3,4-dichlorophenyl)-1-methoxy-1-methylurea; oxadiazon, 2-tert-butyl-4-(2,4-dichloro-5-isopropoxyphenyl)-$\Delta^2$-1,3,4-oxadiazolin-5-one; paraquat, 1,1'-dimethyl-4,4'-bipyridinium ion [as dichloride salts]; atrazine, 2-chloro-4-(ethylamino)-6-(isopropylamino)-s-triazine; barban, 4-chloro-2-butynyl-m-chlorocarbanilate; and cyanazine, 2-[[4-chloro-6-(ethylamino)-s-triazin-2-yl]amino]-2-methylpropionitrile.

One very promising application of this invention relates to the use of liquid formulations containing Dursban ® brand of insecticide to lawns, for the control of insects. Dursban ® brand of insecticide is believed to contain, as its active material, O,O-diethyl O-3,5,6-trichloro-2-pyridyl phosphorothionate (chlorpyrifos).

When the poorly soluble, particulate nitrogen source is melamine or its salts, and granules of melamine, BAM and water soluble binder are made up, the preferred proportions are from 60% to 85% melamine, from 15% to 40% of the soluble binder such as urea, and up to 30% of a BAM. When the granules have been made by using molten urea or the like as the water-soluble binder, the proportions may be from 10% to about 67% melamine, from 33% to 90% urea binder, and again, up to about 30% of the BAM. Thus, overall, the proportions of preferred granules may be from 10% to 85% melamine, from 15% to 90% of the urea binder, and up to 30% of the BAM. Generally the minimum amount of BAM is 1% but it could be less. It must be an effective amount after being placed in the liquid vehicle and applied.

The improved efficacy of liquid herbicidal formulations may take the form of improved weed kill, more prolonged activity, earlier manifestations of activity, lower permissible dosage level of active ingredient, or the like.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A process for herbicidally treating an agricultural substrate, comprising
    applying to said substrate in an agriculturally acceptable liquid:
    (a) a herbicidally active hexazinone material, and
    (b) a melamine component selected from the group consisting of melamine, physiologically acceptable inorganic and organic salts thereof, and mixtures thereof;
    said melamine component being partly dissolved in said liquid, and the undissolved melamine component comprises particles primarily less than 440 micrometers in size that are dispersed in said liquid,
    said herbicidally active hexazinone material being applied at a concentration that is useful and effective for the exertion of its herbicidal activity,
    said herbicidally active hexazinone material and said melamine component being applied to be present on said substrate in such contact that they can coact to improve the efficacy of said herbicidally active hexazinone material.

2. The process of claim 1 wherein urea is also present, dissolved in said liquid.

3. The process of claim 5 wherein said liquid comprises dissolved urea and a dispersant.

4. The process of claim 1 wherein said liquid comprises dissolved or suspended materials providing fertilizer values.

5. A sprayable liquid composition that is characterized by herbicidal and fertilizer activity, comprising
an agriculturally acceptable liquid having dispersed therein sources of N fertilizer values, said N sources comprising at least one poorly water soluble N source having a water solubility at 20° C., at pH 7, not above 5 g per 100 g of water and being selected from the group consisting of melamine, the physiologically acceptable inorganic and organic salts thereof and mixtures thereof wherein the poorly water soluble N source, to the extent not dissolved in said liquid, consists of particles that are suspended in said liquid and that have particle sizes predominantly less than 400 micrometers; and
an agricultural herbicidally active hexazinone material at a concentration useful, upon application of said composition, to perform its intended function; whereby the combination of said poorly water soluble N source and said agricultural herbicidally active hexazinone material, following application of said composition, can coact for the improved efficacy of said agricultural herbicidally active hexazinone material.

6. The composition of claim 5 wherein the ratio of melamine to the material having herbicidal activity is at least 3:1 by weight of melamine to the active herbicidal ingredient.

7. The composition of claims wherein at least a part of said source of N fertilizer values comprises urea.

* * * * *